US00PP11575P

United States Patent [19]

Zary

[11] Patent Number: Plant 11,575

[45] Date of Patent: Oct. 17, 2000

[54] SHRUB ROSE PLANT NAMED 'JACRUWHI'

[75] Inventor: Keith W. Zary, Thousand Oaks, Calif.

[73] Assignee: Bear Creek Gardens, Inc., Medford, Oreg.

[21] Appl. No.: 09/255,058

[22] Filed: Feb. 22, 1999

[51] Int. Cl.[7] ..... A01H 5/00

[52] U.S. Cl. ..... Plt./103

[58] Field of Search ..... Plt./102, 103, 144

*Primary Examiner*—Howard J. Locker

*Attorney, Agent, or Firm*—Klarquist, Sparkman, Campbell, Leigh & Whinston, LLP

[57] ABSTRACT

Shrub rose plant having repeat flowering of white blooms having a strong, clove fragrance; on upright, well-branched growth; and excellent disease resistance.

1 Drawing Sheet

The present invention relates to a new and distinct variety of rugosa rose plant of the shrub class which was originated by me by crossing the variety 'Pirette', (unpatented), with the variety 'Pirette', (unpatented).

The primary objective of this breeding was to examine the variability within the hybrid rugosa variety 'Pirette'. Ripe self-pollinated hips were collected and seed was harvested. A total of 618 seeds were collected and germinated. Several seedlings were selected and propagated by softwood cuttings. 'JACruwhi' was eventually selected as being significantly different and superior to its parent 'Pirette', as evidenced by the following unique combination of characeristics that are outstanding in the new variety and that distinguish it from its parent, as well as from all other varieties of which I am aware:

1. White blooms;
2. Repeat flowering;
3. Upright, well-branched growth;
4. Excellent disease resistance; and
5. Strong fragrance.

'JACruwhi' differs significantly in flower color (White Group 155B versus Red-Purple Group 61C) and petal count (5 petals versus 15–20 petals) from its parent 'Pirette'.

Asexual reproduction of this new rugosa variety by softwood cuttings, as performed at Wasco, Calif., shows that the foregoing and all other characteristics and distinctions come true to form and are established and transmitted through succeeding propagations.

The accompanying illustration shows typical speimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) colour chart, except where ordinary dictionary significance of color is indicated.

Parentage:

*Seed parent.*—'Pirette' (unpatented).

*Pollen parent.*—'Pirette' (unpatented).

Classification:

*Botanical.*—*Rosa rugosa.*

*Commercial.*—Shrub.

FLOWER

Observations made from specimens grown in a garden environment at Somis, Calif., March 1997 to December 1998.

Blooming habit: Continuous.

Bud:

*Size.*—One and one-quarter inches long when the petals start to unfurl.

*Form.*—The bud form is long, pointed ovoid.

*Color.*—When sepals first divide, bud color is a very faint pink, lighter than Red Group 36D. Petals are very fragile, and bruises appear as blemishes. When half blown, the upper and lower sides of the petals are White Group 155B.

*Sepals.*—Color: Green Group 138B. Surface texture: Covered in fine hairs. There are three sepals edged with glands. There are two sepals with hairy edges.

*Receptacle.*—Color: Green Group 137D. Shape: Apple. Size: Medium, about 7/16"×3/8". Surface: Smooth.

*Peduncle.*—Length: Very short, averaging about one inch. Surface: Covered in fine hairs. Color: Yellow-Green group 147D. Strength: Stiff, erect.

Bloom:

*Size.*—Medium to small. Average open size is three inches.

*Borne.*—Singly and several together in flat clusters of three to seven blooms.

*Stems.*—Strength: Strong. Average length is about twelve to sixteen inches.

*Form.*—When first open: Cupped. Permanence:. Retains its form to the end.

*Petalage.*—Number of petals under normal conditions: 5.

*Color.*—The upper sides of the petals are White Group 155B. The reverse sides of the petals are White Group 155B. The base of each petal has a very small (1/8"×1/16"), Yellow Group 2D color spot on both petal surfaces. The major color on the upper side is White Group 155B.

*Variegations.*—None.

*Discoloration.*—The general tonality at the end of the first day: No change. At the end of the third day: Change to White Group 155B from the very faint pink in the bud stage.

*Fragrance.*—Strong, clove.

Petals:

*Texture.*—Thin.

*Shape.*—Oval.

*Form.*—Cupped.

*Arrangement.*—Imbricated. Petaloids in the center: None.

*Persistence.*—Petals drop off cleanly before drying.

*Lastingness.*—On the plant: Short (four to five days). As a cut flower: Short (about five to six days).

Reproductive parts:

*Anthers.*—Size: Medium. Quantity: Many. Color: Yellow Group 13D. Arrangement: Regular around styles.

*Filaments.*—Color: White Group 155B.

*Pollen.*—Color: Not tested.

*Styles.*—Color: Yellow-Green Group 154D. Very short styles.

*Stigmas.*—Color: Yellow-Green Group 154D.

Plant:

*Form.*—Shrub.

*Growth.*—Vigorous, upright, branching. Mature plant height is about three to three and one-half feet, width is about two to two and one-half feet.

Foliage: Number of leaflets on normal mid-stem leaves: Seven or nine.

*Size.*—Large (7" long×4½" wide).

*Quantity.*—Abundant.

*Color.*—New foliage: Upper and lower surfaces: Yellow-Green Group 146C. Old foliage: Upper surface: Green Group 136A. Lower surface: Green Group 136C.

Leaflets:

*Shape.*—Oval.

*Texture.*—Glossy.

*Edge.*—Serrated.

*Serration.*—Single, small.

*Petiole rachis.*—Yellow-Green Group 147C.

*Petiole underside.*—Smooth with prickles.

*Stipules.*—Long (¾"), serrated, bearded.

*Disease resistance.*—Resistant to mildew, rust and blackspot under normal growing conditions in a garden.

Wood:

*New wood.*—Color: Yellow-Green Group 149D. Bark: Smooth.

*Old wood.*—Color: Yellow-Green Group 147C. Bark: Smooth.

Prickles:

*Quantity.*—On main canes from base: Many. On laterals from main canes: Many.

*Form.*—Medium, straight.

*Color when young.*—Yellow-Green Group 147D.

*Color when mature.*—Greyed-Orange Group 165D.

Small prickles:

*Quantity.*—On main stalks: Many. On laterals: Many.

*Color when young.*—Yellow-Green Group 147D.

*Color when mature.*—Greyed-Orange Group 165D.

I claim:

1. A new and distinct variety of rose plant of the shrub class, substantially as herein shown and described, characterized particularly by its repeat flowering of white blooms having a strong, clove fragrance; on upright, well-branched growth; and excellent disease resistance.

* * * * *

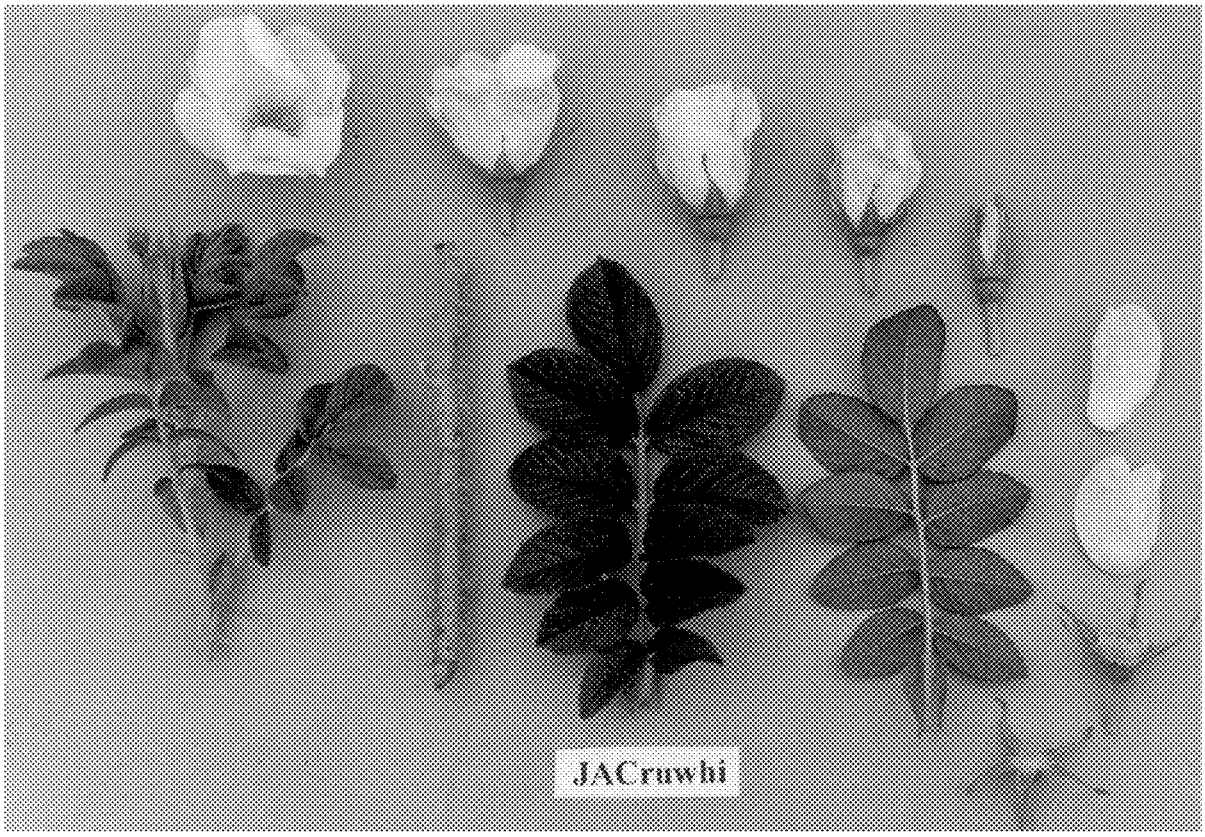
JACruwhi